(12) United States Patent
Miladi

(10) Patent No.: US 9,408,639 B2
(45) Date of Patent: Aug. 9, 2016

(54) SELF-EXTENDING IMPLANT

(71) Applicant: EUROS, La Ciotat (FR)

(72) Inventor: Lotfi Miladi, Bourg la Reine (FR)

(73) Assignee: EUROS, La Ciotat (FR)

( * ) Notice: Subject to any disclaimer, the term of this patent is extended or adjusted under 35 U.S.C. 154(b) by 0 days.

(21) Appl. No.: 14/762,276

(22) PCT Filed: Nov. 20, 2013

(86) PCT No.: PCT/FR2013/052798
§ 371 (c)(1),
(2) Date: Jul. 21, 2015

(87) PCT Pub. No.: WO2014/114853
PCT Pub. Date: Jul. 31, 2014

(65) Prior Publication Data
US 2015/0351805 A1   Dec. 10, 2015

(30) Foreign Application Priority Data
Jan. 23, 2013   (FR) ..................... 13 50585

(51) Int. Cl.
*A61B 17/70* (2006.01)
*A61B 17/72* (2006.01)
A61F 2/30 (2006.01)

(52) U.S. Cl.
CPC ......... *A61B 17/7014* (2013.01); *A61B 17/7025* (2013.01); *A61B 17/7216* (2013.01); *A61F 2002/3052* (2013.01); *A61F 2002/3055* (2013.01); *A61F 2002/30601* (2013.01)

(58) Field of Classification Search
CPC ............. A61B 17/7049; A61B 17/705; A61B 17/7052

USPC .............................. 606/257, 258, 105, 62, 63
See application file for complete search history.

(56) References Cited

U.S. PATENT DOCUMENTS

| 5,516,335 | A | 5/1996 | Kummer et al. |
| 8,715,282 | B2 * | 5/2014 | Pool .................. A61B 17/7216 606/57 |

(Continued)

FOREIGN PATENT DOCUMENTS

| CA | 2 802 078 A1 | 12/2011 |
| WO | 2012/085405 A1 | 6/2012 |

OTHER PUBLICATIONS

International Search Report, dated Jan. 31, 2014, from corresponding PCT application.

*Primary Examiner* — Ellen C Hammond
*Assistant Examiner* — Christina Negrellirodrigue
(74) *Attorney, Agent, or Firm* — Young & Thompson

(57) ABSTRACT

The automatically lengthening implant includes: a body defining internally an axial housing that opens out, at one end, via a mouth and that presents, at its opposite end, a narrowing of section forming an abutment face on the body; an annular plug that is fastened to the mouth of the body and that presents a stop face facing towards the abutment face; at least one rod that is engaged through the annular plug and the body; and a split ring that is mounted on the rod and that is housed in the axial housing of the body. The abutment face and the stop face present shapes that are chamfered, one reentrant and the other projecting, such that the split ring expands on being pressed against the chamfered face of projecting shape and compresses onto the rod when it is pressed against the chamfered face of reentrant shape.

10 Claims, 5 Drawing Sheets

(56) References Cited

U.S. PATENT DOCUMENTS

| | | | |
|---|---|---|---|
| 2007/0213725 A1* | 9/2007 | Hack | A61B 17/7225 606/62 |
| 2009/0030465 A1* | 1/2009 | Altarac | A61B 17/7005 606/257 |
| 2009/0204156 A1 | 8/2009 | McClintock et al. | |
| 2010/0063545 A1 | 3/2010 | Richelsoph | |
| 2013/0338712 A1 | 12/2013 | Massenzio et al. | |

* cited by examiner

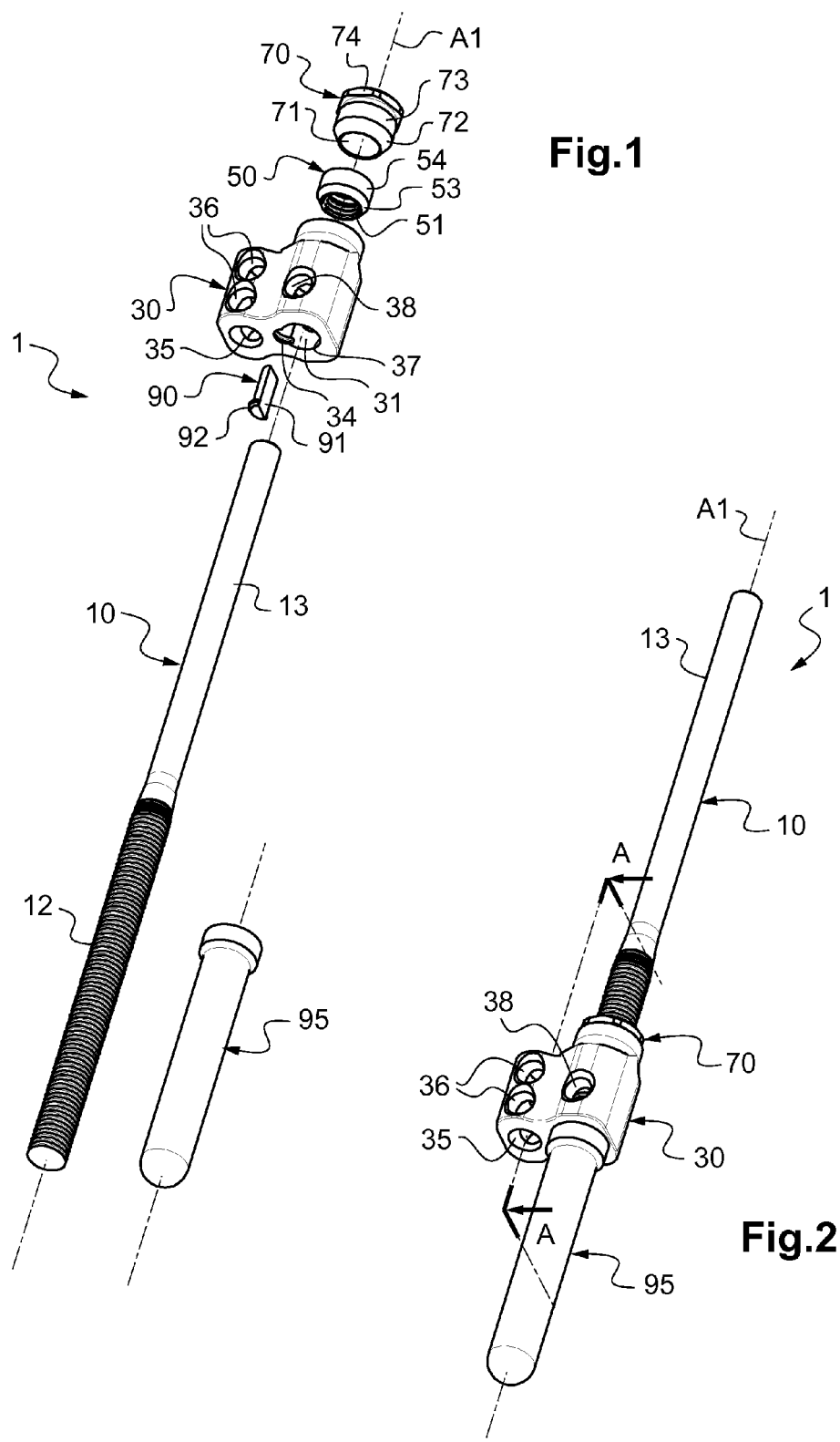

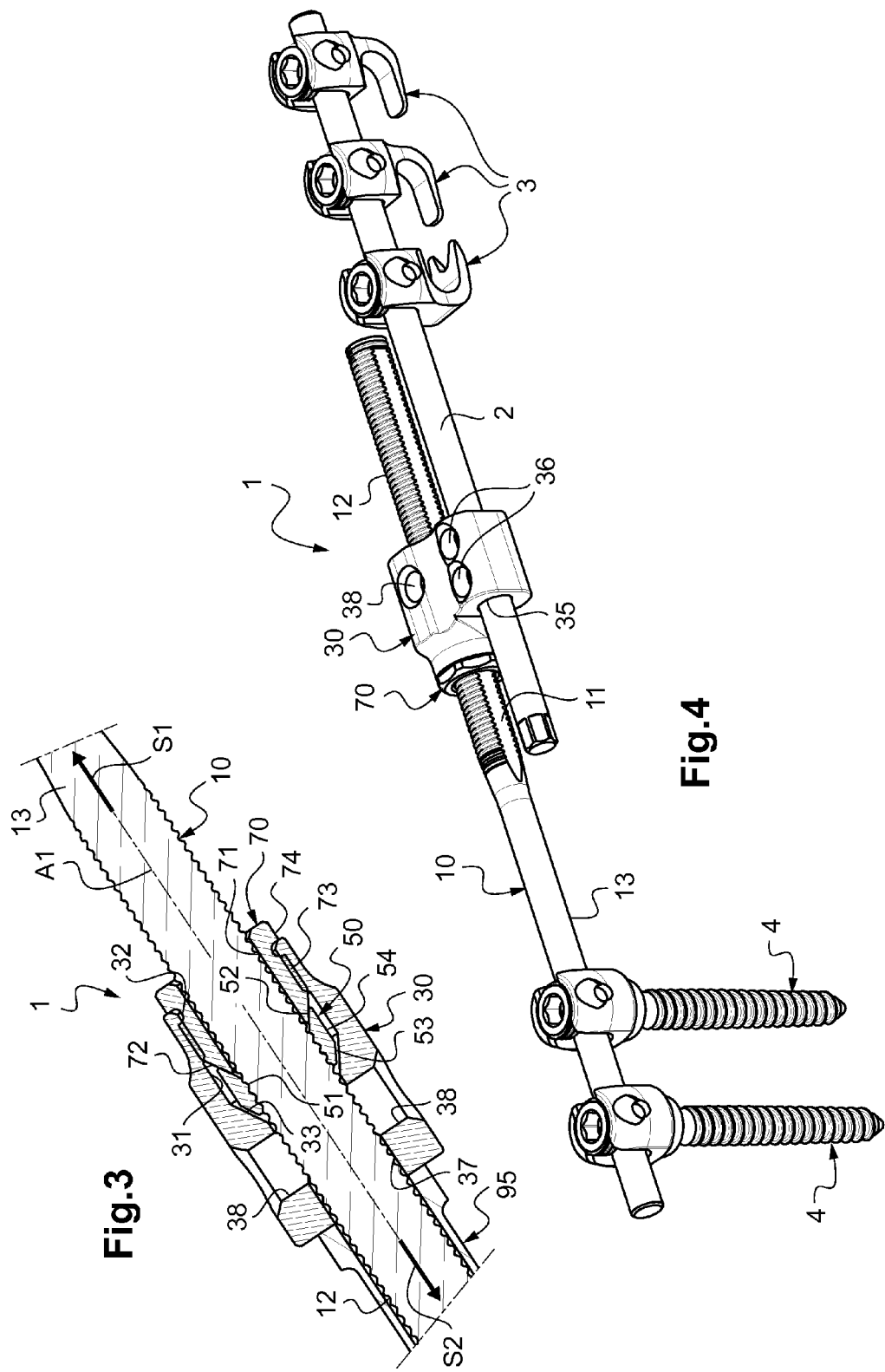

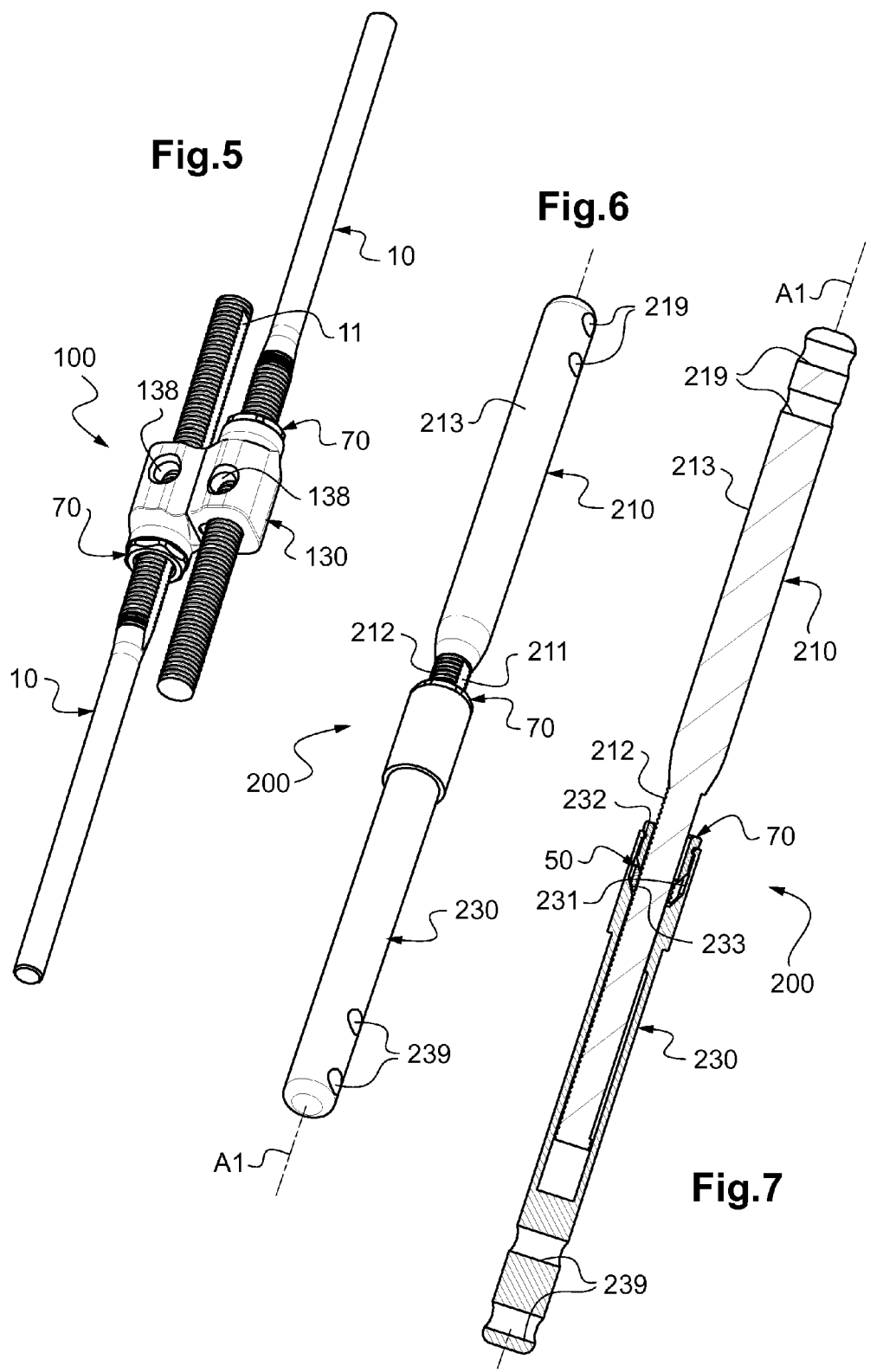

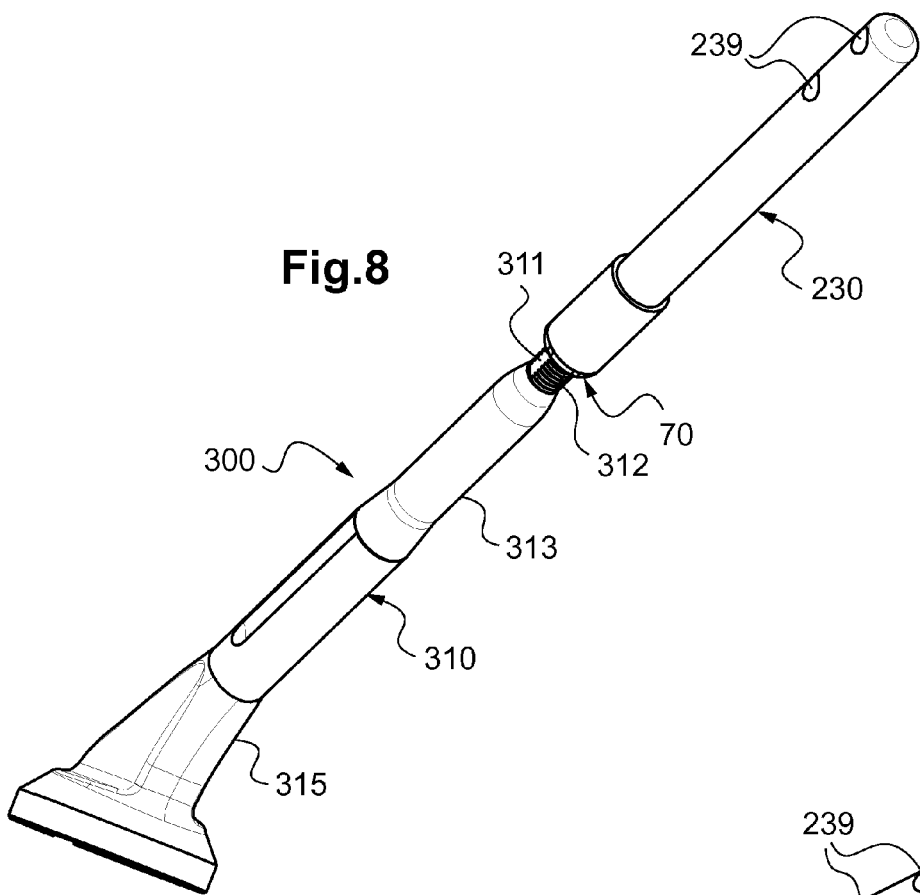
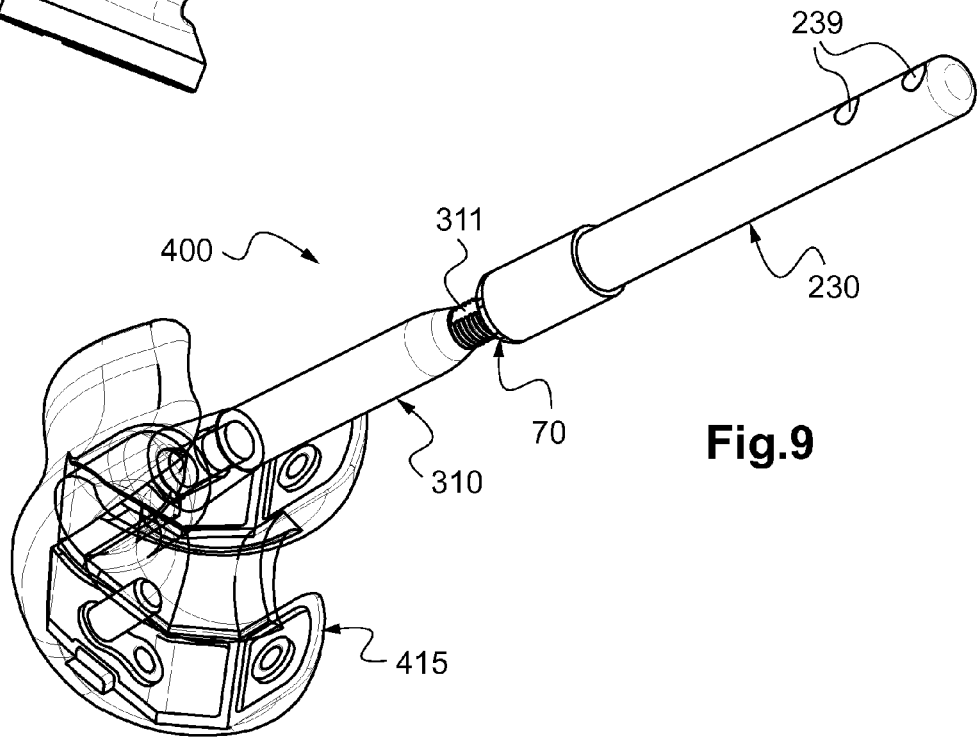

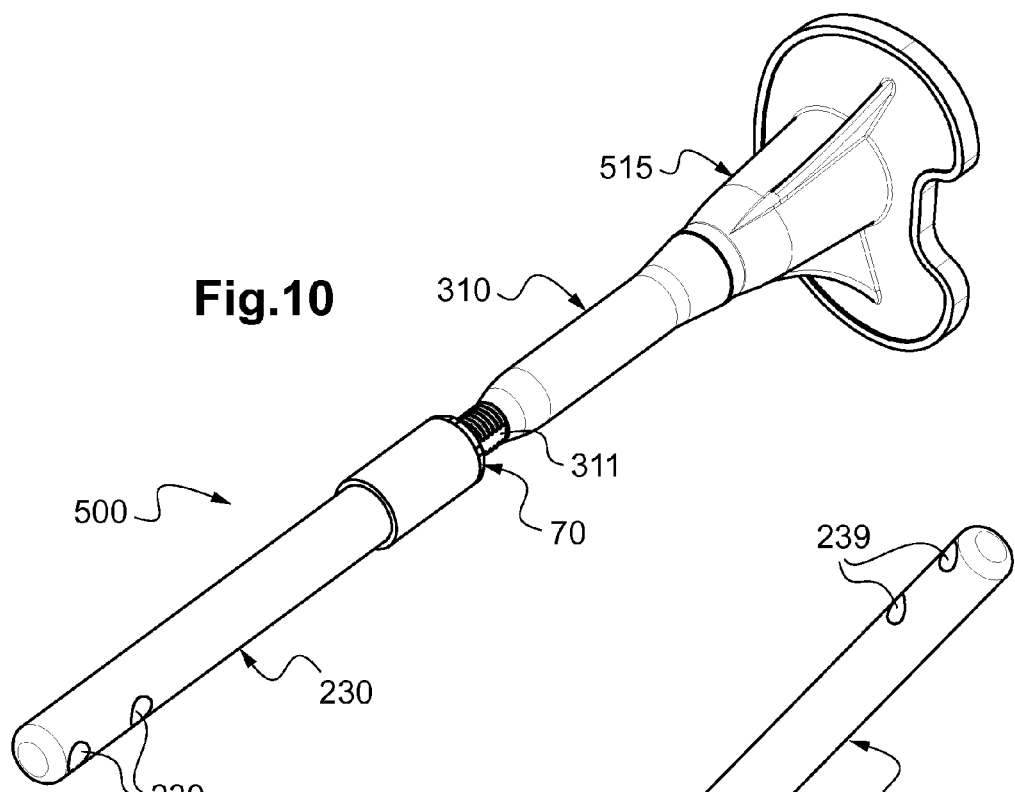
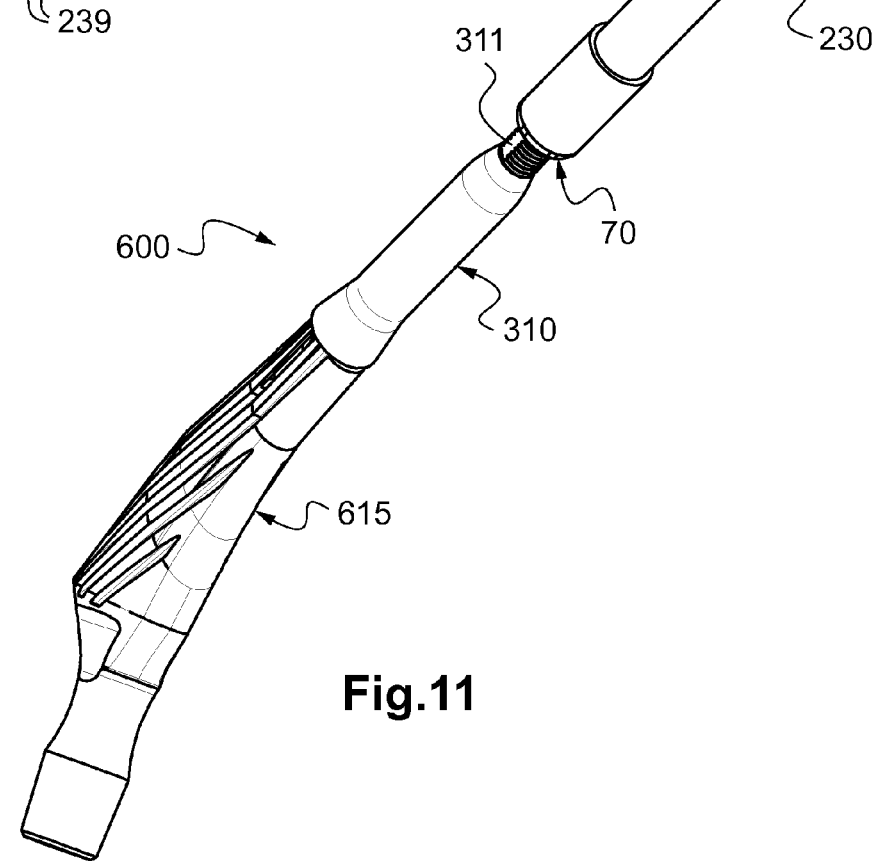

SELF-EXTENDING IMPLANT

TECHNICAL FIELD TO WHICH THE INVENTION RELATES

The present invention relates in general to an implant for fastening to a bone of a young patient.

The invention relates more particularly to an automatically lengthening implant comprising:
- a body defining internally an axial housing that opens out, at one end, via a mouth and that presents, at its opposite end, a narrowing of section so as to form an abutment face on the body;
- an annular plug that is fastened to the mouth of the axial housing of said body and that presents a stop face facing towards said abutment face;
- at least one rod that is engaged through said annular plug and the axial housing of said body; and
- a split ring that is mounted on the rod and that is housed in the axial housing of said body.

A particularly advantageous application of the invention lies in making an implant for connecting together two vertebrae, an implant for connecting together two portions of a long bone, or an implant including a joint prosthesis.

TECHNOLOGICAL BACKGROUND

Operations performed on the bones of young patients often present a common drawback, namely that of subsequently limiting or blocking growth of such bones.

For example, in the event of a tumor being resected at the knee, it is known to replace a portion of the bone and its joint with a prosthesis. Unfortunately, it is the portion of the bone that is situated close to the knee joint that presents the greatest potential for growth. Under such circumstances, the patient's operated leg will lengthen less than the other leg, thereby giving rise to unbalance.

The solution presently used for remedying that problem consists in regularly re-operating the patient so as to lengthen the prosthesis. It can be understood that that solution is not very satisfactory since repeated operations are correspondingly traumatic for the patient, and they also make the patient run risks.

Furthermore, in the event of a major deviation of the vertebral column (scoliosis or kyphosis), it is known to use rigid link rods that serve to straighten the vertebral column. For that purpose, the link rods are curved so as to have appropriate curvature, and then they are blocked parallel to the vertebral column by means of a plurality of hooks and screws fastened to certain vertebrae of the vertebral column. There is then a risk of the link rods preventing any growth of the vertebral column, thus requiring repeated operations every six months in order to lengthen the rods and allow the child's vertebral column to continue growing. Such repeated operations include risks of frequent complications such as vertebrae fusing together, thereby preventing any mobility in the vertebral column.

A known solution for accompanying the lengthening of the vertebral column without a new operation is described in Document US 2009/0204156.

It consists in connecting two parallel rods by a mechanism that leaves the rods free to move in translation when they are pulled apart from each other but that block movement of the two rods when they are pushed towards each other. The implant is thus free to lengthen as the patient grows, but it cannot shorten, so it continues to perform its function of straightening the vertebral column.

The mechanism described in that document comprises a body having two parallel housings passing therethrough, each of which receives one of the two rods. Each housing opens out at one end of the body via a large mouth and presents a section that tapers progressively towards the other end of the body.

A split ring is then mounted on each of the rods and is held inside each housing of the body by a plug. More precisely, each plug is cut so as to form a spring that urges each split ring to press against the narrowing section of each housing of the body.

Thus, when the rods are pushed towards each other, they push the split rings into the narrowing sections of the housings in the body, such that the split rings become compressed onto the rods and block them.

In contrast, when the rods are pulled apart from each other, they pull the split rings away from the narrowing sections in the housings, so that the split rings can expand and release the rods.

The major drawback of that mechanism is its poor reliability over time.

The resilient characteristics of the plugs run the risk of changing over time, so that the implant can no longer perform the function for which it is designed.

An effect of the split rings adhering to the rods is also to be feared, which would make the mechanisms inoperative.

OBJECT OF THE INVENTION

In order to remedy the above-mentioned drawbacks of the state of the art, the present invention proposes an automatically lengthening implant of architecture that is simple, reliable, and compact.

More particularly, the invention provides an implant as defined in the introduction wherein said abutment face and stop face present shapes that are chamfered, one reentrant and the other projecting, and wherein said split ring presents two thrust faces that face respectively towards said abutment face and towards said stop face and that present shapes such that said split ring expands when it is pressed against the chamfered face of projecting shape and compresses against said rod when it is pressed against the chamfered face of reentrant shape.

Thus, by means of the invention, when the rod is pushed in one direction, it pushes the spilt ring against the reentrant face, thereby compressing the split ring onto the rod and thus blocking the rod.

In contrast, when the rod is pulled in the opposite direction, it causes the split ring to press against the projecting face. The projecting shape of that face enables it to force the split ring to expand, thereby releasing the rod to move in translation.

There is no longer any fear of the split ring adhering to the rod.

By means of this architecture, there is also no need for springs, thereby ensuring that the implant continues to be reliable in the long term.

Other characteristics of the implant in accordance with the invention that are advantageous and non-limiting are as follows:
- said thrust faces present shapes that are complementary to said abutment face and said stop face;
- said abutment face and said stop face present conical shapes;
- the inside face of said split ring and at least a portion of the length of said rod present notches that co-operate together;

a pin is provided that is received in a lateral setback of the axial housing and that has a flat pressing against a flat provided correspondingly on the rod;

said annular plug is incompressible;

when the implant is for application to a spine, said axial housing is a through housing and wherein said body defines another through axial housing passing another rod parallel to said rod;

at least one cap is provided that is fastened to said body and that is engaged on a second end of said rod;

when the implant is for application to a long bone, said body is formed by a second rod that is hollow at least in part and that is situated to extend said rod, said rod and said second rod each presenting at least one transverse through hole; and when the implant is for application to a joint, said body is formed by a second rod that is hollow, at least in part, and that is situated extending said rod, one of said rod and said second rod then presenting at least one transverse through hole and the other one of said rod and of said second rod carrying a joint prosthesis at its free end.

DETAILED DESCRIPTION OF AN EMBODIMENT

The description below made with reference to the accompanying drawings, given as non-limiting examples, shows clearly what the invention consists in and how it can be put into practice.

In the accompanying drawings:

FIG. 1 is an exploded diagrammatic perspective view of a first embodiment of an implant of the invention, for application to the vertebral column;

FIG. 2 is an assembled diagrammatic perspective view of the FIG. 1 implant;

FIG. 3 is a diagrammatic axial section view on plane A-A of FIG. 2;

FIG. 4 is an assembled diagrammatic perspective view of the FIG. 1 implant with two screws and three hooks fitted thereto;

FIG. 5 is an assembled diagrammatic perspective view of a variant embodiment of the FIG. 1 implant;

FIG. 6 is a diagrammatic perspective view of a second embodiment of the implant of the invention, for application to a long bone;

FIG. 7 is a diagrammatic section view of the FIG. 6 implant;

FIG. 8 is a diagrammatic perspective view of a third embodiment of the implant of the invention, forming a humeral shoulder prosthesis;

FIG. 9 is a diagrammatic perspective view of a fourth embodiment of the implant of the invention, forming a femoral knee prosthesis;

FIG. 10 is a diagrammatic perspective view of a fifth embodiment of the implant of the invention, forming a tibial knee prosthesis; and FIG. 11 is a diagrammatic perspective view of a sixth embodiment of the implant of the invention, forming a femoral hip prosthesis.

As a preliminary point, it should be observed that elements that are identical or similar in the different variants and embodiments of the invention shown in the various figures are, wherever possible, given the same reference signs and they are not described each time.

FIGS. 1 to 11 show six embodiments of an automatically lengthening implant 1; 100; 200; 300; 400; 500; 600 for fastening in or on a bone of a young patient.

In these six embodiments, the implant is designed to accompany or support growth of the bone to which it is fitted.

As shown in the figures, this automatically lengthening implant 1; 100; 200; 300; 400; 500; 600 has four main components, namely a movable rod 10; 110; 210; 310, a body 30; 130; 230, an annular plug 70, and a split ring 50.

The movable rod 10; 110; 210; 310 is designed to be fastened in or on the patient's bone.

The body 30; 130; 230, the annular plug 70, and the split ring 50 are designed to enable the implant to lengthen when a traction force is exerted on the movable rod 10; 110; 210; 310, and to avoid any shortening of the implant when a compression force is exerted on the movable rod 10; 110; 210; 310.

For this purpose, the body 30; 130; 230 defines internally at least one axial housing 31; 231 of axis A1 that receives the split ring 50, this axial housing opening out at one end via a large mouth 32; 232 and presenting a section narrowing forming an abutment face 33; 233 (see FIGS. 3 and 7) for the split ring 50.

The annular plug 70 is fastened in the mouth 32; 232 of the axial housing 31; 231 of the body 30; 130; 230 and presents a stop face 72 facing towards the above-mentioned abutment face 33; 233 (see FIG. 3) in order to retain the split ring 50 in the axial housing 31; 231.

The rod 10; 110; 210; 310 is threaded through the annular plug 70, the split ring 50, and the axial housing 31; 231 of the body 30; 130; 230.

According to a particularly advantageous characteristic of the invention, the abutment face 33; 233 and the stop face 72 present chamfered shapes one reentrant and the other projecting, and the split ring 50 presents two thrust faces 52, 53 that face respectively towards the abutment face 33; 233 and the stop face 72.

A face is said herein to be of "projecting" shape when each axial section of the face forms a dihedral angle that is acute.

A face is said herein to be of "reentrant" shape when each axial section of the face forms a dihedral angle that is obtuse.

In this example, the face of projecting shape is formed by the stop face 72 of the annular plug 70, while the face of reentrant shape is formed by the abutment face 33; 233 of the body 30; 130; 230.

Thus, when a traction force is applied on the rod 10; 110; 210; 310 (in the direction S1 in FIG. 3), this force brings the thrust face 52 of the split ring 50 against the stop face 72 of the annular plug 70, thereby enabling the split ring 50 to be expanded and thus releasing the rod.

In contrast, when a compression force is applied to the rod 10; 110; 210; 310 (in the direction S2 in FIG. 3), this force brings the other thrust face 52 of the split ring 50 against the abutment face 33; 233 of the body 30; 130; 230, thereby serving to compress the split ring 50 against the rod, which is then blocked.

In this example, and in preferred manner, the thrust faces 52, 53 present shapes that are complementary to the abutment faces 33; 233 and the stop face 72.

Advantageously, the thrust faces 52, 53 of the split ring 50, the abutment face 33; 233 of the body 30; 130; 230, and the stop face 72 of the annular plug 70 then present frustoconical surfaces of revolution around the axis A1. In this example, all of these frustoconical faces also present the same angle at the apex, of the order of 60 degrees.

In FIGS. 1 to 4, there can be seen more particularly a first embodiment of the automatically lengthening implant 1.

In this embodiment, the implant constitutes a connection system 1 enabling a surgeon to block at least one vertebra of a vertebral column of a young patient relative to another vertebra or relative to the patient's pelvis.

The connection system 1 is used in particular for straightening the vertebral column of the patient when it presents pronounced kyphosis or scoliosis.

As shown in FIG. 4, the connection system 1 has two rods, including the above-mentioned movable rod 10 and a stationary rod 2.

In addition to the above-described axial housing 31, the body 30 then also has a duct 35 of axis parallel to the axis A1 of the axial housing 31. In this example, both the axial housing 31 and the duct 35 pass through the body and serve respectively to pass the movable rod 10 and the stationary rod 2.

One of the two rods, in this example the stationary rod 2, is designed to be provided with three hooks adapted to be fastened to three of the patient's cervical or dorsal vertebrae, while the other one of the two rods, in this example the movable rod 10, is provided with two screws 4 suitable for being screwed into the pedicles of the patient's lumbar vertebrae.

This can be referred to as a "suspended assembly" in the sense that the cervical or dorsal vertebrae are suspended from the free end of the stationary rod 2.

In this example, the stationary rod 2 is in the shape of a cylindrical body of revolution with an outside surface that is smooth.

It is made as a single piece of titanium.

The movable rod 10 has a smooth half 31 in the form of a cylindrical body of revolution about the axis A1 and of diameter substantially equal to the diameter of the stationary rod 2, and a notched half 12 forming a body of revolution about the axis A1 and of greater diameter.

As can be seen in FIG. 3, the notches are formed by a regular succession of convex and concave shapes, each forming a projecting rounded rib or a recessed curved groove on the movable rod 10.

In this example, and as shown more particularly in FIG. 4, the notched half 12 of the movable rod 10 presents a lateral flat 11 that extends along its entire length.

As shown in FIG. 1, the body 30 is generally in the form of a rectangular parallelepiped having the axial passage 31 for passing the movable rod 10, and also the duct 35 for passing the stationary rod 2 passing through it in its long direction.

As can be seen in FIG. 4, the duct 35 presents a diameter that is equal, ignoring assembly clearance, to the diameter of the stationary rod 2. It thus enables the stationary rod 2 to be guided to move in translation along an axis parallel to the axis A1.

The body 30 then presents two tapped bores 36 of axes perpendicular to the axis of the duct 35 and each of which opens out at one end to the outside and at the other end into the duct 35.

These two tapped bores 36, which are juxtaposed side by side in this example, serve in particular to receive two screws (not shown) so that their ends can press against the stationary rod 2 in order to block it in the duct 35.

The mouths of these two tapped bores 36 are chamfered in this example in order to receive the heads of the screws so that the screws do not emerge outside the body 30.

As can be seen in FIG. 3, the axial housing 31 opens out at opposite ends of the body 30, at one end via the large mouth 32 and at the other end via an outlet 37 of smaller diameter.

The narrowing of section in the axial housing 31 that forms said abutment face 33 in the body 30 is situated in this example halfway along the axial housing 31. The remainder of the axial housing 31 presents a section of constant diameter.

Thus, a first portion of the axial housing 31, the portion situated between the outlet 37 and the narrowing of section, presents a constant diameter that is equal, ignoring assembly clearance, to the outside diameter of the notched half 12 of the movable rod 10. In this way, the first portion of the axial housing 31 contributes to guiding movement of the movable rod 10 in translation along the axis A1.

The other portion of the axial housing 31, i.e. the portion situated between the mouth 32 and the narrowing of section, presents a diameter that is greater than the diameter of the movable rod 10, thereby enabling it to receive the split ring 50 and the annular plug 70.

As shown in FIGS. 1 to 4, the body 30 also presents two other tapped bores 38, of axes perpendicular to the axis A1, each of which bores opens out at one end to the outside and at the other end into the first portion of the axial housing 31. In this example, these two tapped bores 38 lie on the same axis, and therefore open out facing each other inside the axial housing 31.

These two tapped bores 38 serve to receive two screws (not shown) so that their ends can press against opposite sides of the movable rod 10 in order to block it in the axial housing 31.

In this example, the mouths of these two tapped bores 38 are likewise chamfered for receiving the heads of these screws so that the heads do not emerge outside the body 30.

In this example, the body 30 is made as a single piece of titanium.

The annular plug 70 is substantially in the form of a body of revolution about the axis A1.

It thus presents a central duct 71 forming a cylindrical surface of revolution about the axis A1 that is smooth in order to pass the movable rod 10. This central duct 71 presents a diameter that is equal, ignoring assembly clearance, to the outside diameter of the notched half 12 of the movable rod 10. It thus contributes to guiding the movement of this movable rod 10 in translation along the axis A1.

The annular plug 70 presents a threaded outside face 73 that enables it to be screwed into the tapped mouth 32 of the axial housing 31 in the body 3.

The annular plug 70 is then bordered on the outside, at one end, by a ring 6 having hexagonal flats enabling it to be securely tightened in the mouth 32 by means of a tool provided for this purpose (of the pipe wrench type).

The opposite end of the annular plug 70, which constitutes said stop face 72, presents a projecting chamfered shape.

In this example, the annular plug 70 is made as a single piece of titanium, so as to be undeformable and incompressible.

As can be seen in FIGS. 1 and 3, the split ring 50 is generally in the shape of a tube of axis A1 that is split longitudinally.

It thus presents a cylindrical outside face 54 that is substantially a surface of revolution about the axis A1. It also presents an inside face 51 that is substantially a surface of revolution about the axis A1, and in this example it is notched so as to be capable of meshing with the notches of the movable rod 10. Finally, it presents two end faces, one of projecting shape and the other of reentrant shape, which form said thrust faces 52, 53.

The split in the split ring 50 enables it to be compressed radially or to be expanded radially around the axis A1. This split presents a width such that, when the split ring 50 is compressed and the two edges of the split meet, the inside face 51 of the split ring 50 presents a mean diameter that is less than the mean diameter of the notched half 12 of the movable rod 10.

In this example, the split ring 50 is made as a single piece of titanium.

In advantageous manner, and as shown in FIG. 1, the connection system 1 also has a pin 90 and a cap 95.

The pin 90 serves to prevent any rotation of the movable rod 10 relative to the body 30 about the axis A1.

It is semicylindrical in shape, so it has a plane face that defines a flat 91.

It is adapted to be received in a lateral setback 34 of complementary shape recessed in the axial housing 31 at the same end as the outlet 37 from the axial housing 31.

Thus, once the pin 90 is received in the lateral setback 34, the movable rod 10 can be engaged in the axial housing 31 only in such a manner that its flat 11 bears against the flat 91 of the pin 90, thus blocking any subsequent movement in rotation of the movable rod 10 about the axis A1.

In order to hold the pin 90 in the lateral setback 34, one of the ends of the pin 90 is bordered, on its face opposite from the flat 91, by a semi-circular ridge 92 that is received in a complementary groove provided in the lateral setback 34.

As shown in FIGS. 1 to 3, the cap 95 presents the shape of a tube that is open at one end and closed at its opposite end by a hemispherical wall.

Its open end is fastened around the outlet 37 from the axial housing 31 (e.g. by welding or by adhesive), so as to protect the notched half 12 of the movable rod 10. Thus, no flesh becomes deposited between the notches of the movable rod 10, thereby enabling these notches to co-operate cleanly with the notches of the split ring 50.

The cap 95 presents an inside diameter that is equal, ignoring assembly clearance, to the outside diameter of the notched half 12 of the movable rod 10, so that it participates in guiding movement of the movable rod 10 in translation along the axis A1.

In this example, it is made as a single piece of titanium.

The connection system 1 is delivered so that it presents a short length, i.e. in such a manner that its notched half 12 extends very little from the mouth 32 of the axial housing 31 of the body 30. It thus presents a large reserve for lengthening.

It is delivered with two screws tightened in the tapped bores 38 to prevent the movable rod 10 from moving in the body 30.

This connection system 1 is put into place relative to the screws 4 and the hooks 3 (that have previously been fastened to the pedicles of the patient's lumbar vertebrae and to the patient's cervical or dorsal vertebrae) without loosening these screws so that the movable rod 10 remains blocked in position.

Nevertheless, this putting into place requires the shape and the length of the connection system 1 to be adjusted.

Its shape is then adjusted by appropriately curving the stationary rod 2 and the smooth portion 13 of the movable rod 10, thereby providing regular curvature to the connection system 1 overall.

Its length is adjusted by cutting the stationary rod 2 to the desired length, without using up the potential for lengthening of the movable rod 10, thus enabling the entire notched half 12 of the movable rod 10 to act as a reserve for growth.

At the end of this operation of putting the connection system 1 into place on the screws 4 and the hooks 3, the screws tightened in the tapped bores 38 of the body 30 can either be left in place or else removed by the surgeon.

When they are left in place, these screws prevent any automatic lengthening of the connection system 1. Subsequent operations will therefore be necessary for lengthening it by loosening and then retightening the screws. The connection system 1 is nevertheless still useful since, during each of these subsequent operations, the split ring 50 ensures that the connection system 1 cannot shorten.

In contrast, if these screws are removed by the surgeon, then the connection system 1 can follow the growth of the patient's vertebral column automatically, lengthening progressively as growth proceeds. This lengthening may optionally be driven (without any surgical operation) by asking the patient to perform particular stretching movements of the torso, possibly with the help of a third person.

FIG. 5 shows a variant embodiment 100 of the connection system shown in FIGS. 1 to 4.

In this variant, the connection system 100 does not have one, but rather two, movable rods 10 that are identical to the movable rod shown in FIG. 1.

The body 130 then does not define one, but rather two housings that are identical and parallel, with their mouths facing in opposite directions.

Each of these housings then receives a respective split ring, an annular plug 70, and a pin that are identical to those shown in FIG. 1.

The body 130 also has two pairs of tapped bores 138 suitable for receiving screws that serve to lock both of the movable rods 10 in fixed positions.

In this variant, the potential of the connection system 100 for lengthening is twice that of the connection system 1 shown in FIGS. 1 to 4.

FIGS. 6 and 7 show a second embodiment of the automatically lengthening implant 200 of the invention.

In this embodiment, the implant constitutes a link shaft 200 enabling a surgeon to connect together two portions of a long bone.

The term "long bone" is used to mean any type of bone of length that is much greater than its mean diameter (e.g. the tibia, the humerus, the metacarpal bones, . . . ).

In this embodiment, the movable rod 210 has a notched half 212 identical to the notched half 12 of the movable rod 10 shown in FIG. 1. In contrast, its smooth half 213 is of a different diameter (in this example greater than the diameter of the notched portion 212), that matches the diameter of the medullary canal of the bone in which it is to be engaged.

In this example, the body 230 of this link shaft 200 is in the form of a rod of diameter identical to the diameter of the smooth half 213 of the movable rod 210.

In this example, the axial housing 231 provided inside the body 230 for receiving the notched half 212 of the movable rod 210 opens out solely at one end of the body 230. At its mouth 232, it presents a shape identical to that of the axial housing 31 of the body 30 shown in FIG. 1. In contrast, the housing extends inside the body 230 so that the body 230 performs the function of a protective cap.

The axial housing 231 receives a split ring 50, an annular plug 70, and a pin identical to those shown in FIG. 1.

For fastening to the bone, the movable rod 210 and the body 230 present respective pairs of through holes 219, 239 of axes perpendicular to the axis A1 of the movable rod 210. These through holes 219, 239 thus enable the movable rod 210 and the body 230 to be fastened to the two portions of the bone by means of screws.

The link shaft 200 can thus be used with a long bone for the purpose of lengthening it.

For this purpose, the bone is cut into two portions, the movable rod 210 then being engaged in the medullary canal of one of these portions, while the body 230 is engaged in the medullary canal of the other portion of the bone.

They are then fastened therein by nails.

The bone is then lengthened progressively, e.g. by about 1 millimeter per day, so that the two portions of the bone can join together but without having the time to solidify (advantage is thus taken of the consolidation period of the bone in order to lengthen it).

FIGS. 8 to 11 show other embodiments of the invention, in which the automatically lengthening implant presents a joint prosthesis function.

Thus, in FIG. 8, there is shown a third embodiment 300 of the automatically lengthening implant of the invention.

In this embodiment, the implant presents a humeral prosthesis function for the shoulder.

Its body is identical to the body 230 described with reference to FIG. 6. It is thus suitable for being fastened in the medullary canal of the patient's humerus and to receive a split ring 50, an annular plug 70, and a pin identical to those shown in FIG. 1.

In contrast, its rod 310 is of a shape different from those described above.

In this embodiment, the movable rod 310 also has a notched half 312 identical to the notched half 12 of the movable rod 10 shown in FIG. 1. However its smooth half 313 presents a diameter that increases going towards its free end.

Furthermore, recessed in its free end, it also presents a conical housing suitable for having a shoulder prosthesis 315 fastened therein.

FIGS. 9 to 11 show respectively fourth, fifth, and sixth embodiments 400; 500; 600 of the automatically lengthening implant of the invention.

In these embodiments, the implant presents respectively a femoral prosthesis function for the knee, a tibial prosthesis function for the knee, and a femoral prosthesis function for the hip.

In these three embodiments, the body 230, the movable rod 310, the split ring 50, the annular plug 70, and the pin are identical to those of the implant shown in FIG. 8.

Only the joint prosthesis fastened in the conical housing of the movable rod 310 differs. As can be seen respectively in FIGS. 9 to 11, the prosthesis is then a femoral prosthesis 415 for the knee, a tibial prosthesis 515 for the knee, or a femoral prosthesis 615 for the hip.

The present invention is not limited in any way to the embodiment described and shown, and the person skilled in the art will know how to apply any variant in compliance with its spirit.

It particular, provision may be made for one and/or the other of the components of the automatically lengthening implant to be made of a plastics material (in particular of polyetheretherketone (PEEK)), or out of composite material (e.g. based on carbon fibers embedded in a PEEK matrix).

In another variant, provision could be made for the annular plug to be screwed, not into the inside of the mouth of the body, but onto its outside so as to cover it. Provision could also be made to fasten it thereto in some other way, e.g. by adhesive or by welding.

In another variant, provision could be made for the abutment, stop, and thrust faces to present shapes other than conical surfaces of revolution, e.g. they could present pyramid shapes. Provision could also be made for the split ring to present an annular shape of circular section.

Also in a variant, provision could be made for the movable rod and for the split ring not to be notched, but to be completely smooth, in which case the blocking of the movable rod would nevertheless be less reliable.

Provision could also be made for the notches to present sections that are not in the form of regular waves, but for example sections in the form of triangles (which would make it easier for the split ring to pass from one notch to another in one direction while preventing it from moving in the opposite direction).

The invention claimed is:

1. An automatically lengthening implant comprising:
a body defining internally an axial housing that opens out, at one end, via a mouth, and that presents a narrowing of section so as to form an abutment face on the body;
an annular plug that is fastened to the mouth of the axial housing of said body and that presents a stop face facing towards said abutment face;
at least one rod that is engaged through said annular plug and the axial housing of said body; and
a split ring that is mounted on the rod and that is housed in the axial housing of said body;
wherein said abutment face and stop face present shapes that are chamfered, one reentrant and the other projecting, and in that said split ring presents two thrust faces that face respectively towards said abutment face towards said stop face and that present shapes such that said split ring expands radially when it is pressed against the chamfered face of projecting shape and compresses radially against said rod when it is pressed against the chamfered face of reentrant shape.

2. The automatically lengthening implant according to claim 1, wherein said thrust faces present shapes that are complementary to said abutment face and said stop face.

3. The automatically lengthening implant according to claim 1, wherein said abutment face and said stop face present conical shapes.

4. The automatically lengthening implant according to claim 1, wherein the inside face of said split ring and at least a portion of the length of said rod present notches that cooperate together.

5. The automatically lengthening implant according to claim 1, wherein a pin is received in a lateral setback of the axial housing and has a flat pressing against a flat provided correspondingly on the rod.

6. The automatically lengthening implant according to claim 1, wherein said annular plug is incompressible.

7. The automatically lengthening implant according to claim 1 for application to a spine, wherein said axial housing is a through housing and wherein said body defines another through axial housing passing another rod parallel to said rod.

8. The automatically lengthening implant according to claim 7, wherein at least one cap is fastened to said body and is engaged on a second end of said rod.

9. The automatically lengthening implant according to claim 1, for application to a long bone, wherein said body is formed by a second rod that is hollow at least in part and that is situated to extend said rod, said rod and said second rod each presenting at least one transverse through hole.

10. The automatically lengthening implant according to claim 1 for application to a joint, wherein said body is formed by a second rod that is hollow, at least in part, and that is situated extending said rod, and wherein one of said rod and said second rod presents at least one transverse through hole and the other one of said rod and of said second rod carries a joint prosthesis at its free end.

* * * * *